United States Patent [19]

Barnaby

[11] Patent Number: 4,562,726
[45] Date of Patent: Jan. 7, 1986

[54] METHOD AND APPARATUS FOR TESTING THE COMPRESSIBILITY OF SUBTERRANEAN SAMPLES

[75] Inventor: Harold T. Barnaby, Duncanville, Tex.

[73] Assignee: Core Laboratories, Inc., Dallas, Tex.

[21] Appl. No.: 626,631

[22] Filed: Jul. 2, 1984

[51] Int. Cl.[4] ........................................... G01N 15/08
[52] U.S. Cl. ........................................... 73/38; 73/820
[58] Field of Search ...................... 73/38, 820, 825, 37

[56] References Cited

U.S. PATENT DOCUMENTS

| | | |
|---|---|---|
| 2,352,835 | 4/1944 | Hertel . |
| 2,705,418 | 7/1955 | Reichertz . |
| 2,867,116 | 1/1959 | Arowofsky et al. ............ 73/38 |
| 2,874,565 | 2/1959 | Kelton ............................. 73/38 |
| 3,018,660 | 1/1962 | Schmid ........................... 73/38 |
| 3,199,341 | 8/1965 | Heuer, Jr. et al. ............. 73/820 |
| 3,436,955 | 5/1969 | Wilcher . |
| 3,457,777 | 4/1969 | Nielsen . |
| 3,505,860 | 7/1970 | Bishop . |
| 3,616,685 | 11/1971 | Strom . |
| 3,635,078 | 3/1972 | Wissa . |
| 3,820,385 | 6/1974 | Cordoba . |
| 3,839,899 | 10/1974 | McMillen . |
| 3,881,345 | 8/1975 | Souder . |
| 3,975,950 | 12/1976 | Erdei . |
| 4,253,327 | 3/1981 | Wiley ............................. 73/38 |
| 4,487,056 | 12/1984 | Wiley ............................. 73/83 |

Primary Examiner—Stewart J. Levy
Assistant Examiner—Hezron E. Williams
Attorney, Agent, or Firm—Lee C. Robinson, Jr.

[57] ABSTRACT

Compressibility test apparatus and method of testing compressibility. The apparatus includes a holder having a sample chamber for holding a sample in the environment of a confining pressure and means for supplying an internal pressure to the held sample. The sample and various conduits and channels that communicate with the sample define an internal system volume. Connected in this internal system volume is an internal volume adjustment pump that is operable to vary the internal system volume in incremental steps, by which the internal pressure is reduced (or increased) in steps to increase (or reduce) the net confining pressure. As a result, changes in the sample volume as a function of changes in the net confining pressure are determined, from which the compressibility of the sample is obtained.

28 Claims, 3 Drawing Figures

METHOD AND APPARATUS FOR TESTING THE COMPRESSIBILITY OF SUBTERRANEAN SAMPLES

BACKGROUND OF THE INVENTION

This invention relates to a method and apparatus for testing the compressibility of a sample, such as a subterranean core sample.

In the field of geological exploration for sources of petroleum reserves, natural gas formations, and the like, relatively accurate predictions of the type and quantity of such reserves may be obtained by analyzing samples derived from the subterranean formation. For example, if a core sample from the subterranean formation is obtained and analyzed for its compressibility and permeability, generally accurate indications may be made regarding the quantity of petroleum that may be present in a subterranean reservoir, the degree of difficulty involved in extracting the petroleum, the ability of the subterranean formation to support the various mechanical devices which are used to extract the petroleum, and the like.

Various techniques are known for testing or measuring the compressibility of core samples derived from the aforementioned subterranean formations. For example, the core sample may be placed in a testing chamber subjected to a relatively high pressure, and an axial load may be applied to the same by, for example, driving a mechanical plate downward onto the sample. The driving force may be generated by a pressure-activated piston, and sensing elements, such as strain gauges, have been used to determine the axial change in sample length at various loading conditions. Compressibility is determined as function of strain or length reduction, compared to the original sample length.

In another technique for measuring compressibility (and one in which the present invention finds ready application), a completely liquid-saturated core sample is placed in a chamber and a high confining pressure is applied to all surface areas of the sample, resulting in a condition of multiple-axis loading analogous to overburden loading in a natural reservoir. Another pressure source, in communication with the internal saturated pore-space of the sample only, is used to control the ratio of pore-space pressure to overburden sample-loading pressure, giving a direct measurement of net confining pressure.

In an untapped natural reservoir, the pore-space pressure and overburden loading pressure are in equilibrium: the combined hydraulic pressure of the pore-space fluid and the mechanical strength of the rock is equal to the overburden force imposed by the overhead rock structure. As fluids are withdrawn from the reservoir during production, there is a corresponding loss in hydraulic pore pressure, transferring a greater proportion of the overburden load to the rock structure. As the strength of a porous rock material depends in part on the area of contact between the individual grains within the matrix, a reduction in pore pressure will cause grain slippage to a point where the increased grain contact area provides a propping strength equal to the loss in hydraulic pore pressure. The resulting compressibility effect results in a corresponding reduction in pore volume as grains of material are driven into closer contact. Therefore, pore volume reduction and rock compressibility can be accurately determined by measuring the volume of fluid displaced from the saturated pore space, as a function of differential pressure.

Accurate measurement of the small volume of fluid displaced from the sample pore space may be achieved by withdrawing a small, uniform diameter rod inserted into a plumbing system connected to the pore space fluid chamber, to which a means for measuring pressure is included. A rod of known diameter withdrawn a known length provides a known volume in which pore fluid can be displaced. The resulting pore pressure is measured by the pressure reading devices, after grain deformation is complete and the sample has reached equilibrium. The resulting fluid displacement is compared with the total pore space volume of the sample for determination of compressibility at a known loading condition.

One disadvantage of compressibility testing devices of the aforenoted type, using a moving piston of small diameter and considerable length, essential to accurate volume determination, is the risk of having the piston buckle because of the compressional force exerted on it by the high fluid pressure applied to the pore space.

OBJECTS OF THE INVENTION

Therefore, it is an object of the present invention to provide an improved method and apparatus to test the compressibility of a sample, such as a subterranean rock sample.

Another object of this invention is to provide apparatus of the aforementioned type, including an internal volume adjust pump, and a method of using same.

A further object of this invention is to provide an internal volume adjustment pump, as aforesaid, having a movable piston that is not easily subject to buckling.

An additional object of the present invention is to provide an internal volume adjustment pump having a differential piston for increasing or decreasing the internal system volume of rock compressibility test apparatus.

Various other objects, advantages and features of the present invention will become readily apparent from the ensuing detailed description, and the novel features will be particularly pointed out in the appended claims.

SUMMARY OF THE INVENTION

In accordance with this invention, compressibility test apparatus includes a holder having a sample chamber for holding a sample in the environment of a confining pressure and means for supplying an internal pressure to the held sample. The sample and various conduits and channels that communicate with the sample define an internal system volume. Connected in this internal system volume is an internal volume adjustment pump that is operable to vary the internal system volume in incremental steps, by which the internal pressure is reduced (or increased) in steps to increase (or reduce) the net confining pressure. As a result, changes in the sample pore volume as a function of changes in the net confining pressure are determined, from which the compressibility of the sample is obtained.

Preferably, the internal volume adjustment pump is comprised of a differential piston having two sections of different cross-sectional area, the section of smaller area being driven into a channel and the section of larger area being driven out to increase the effective volume of that channel. The section of smaller area is subjected to tension rather than compression, thereby reducing the likelihood of buckling.

A method of using the aforementioned apparatus to measure the compressibility of a sample also is disclosed.

BRIEF DESCRIPTION OF THE DRAWINGS

The following detailed description, given by way of example, and not intended to limit the present invention solely to the described embodiment, will best be understood in conjunction with the accompanying drawings in which.

DETAILED DESCRIPTION OF A CERTAIN PREFERRED EMBODIMENT

Figure 1:
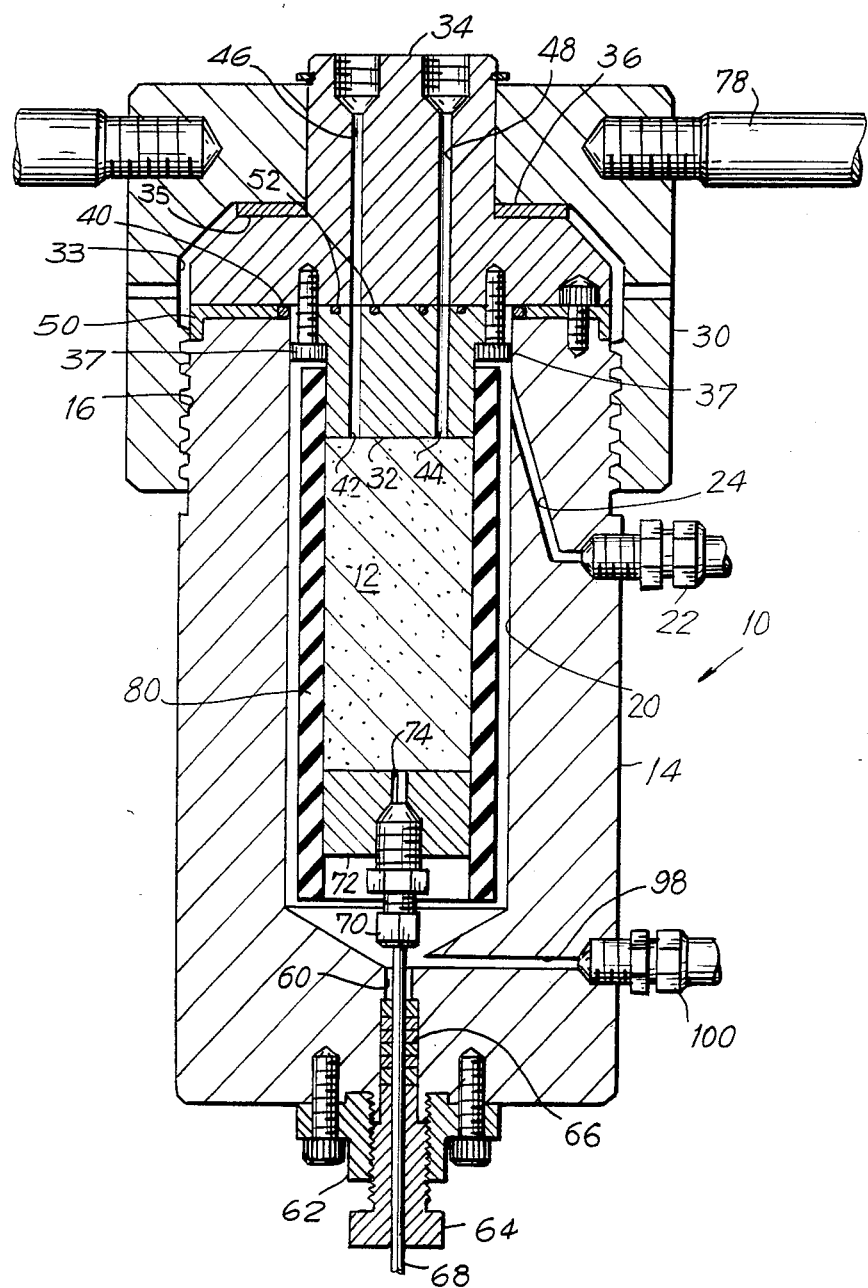
FIG. 1 is a sectional view of a core holder which can be used with the present invention.

Referring now to the drawings, and in particular to FIG. 1, there is illustrated one embodiment of core holder 10 in accordance with the teachings of the present invention. For the purpose of the present discussion, core holder 10 will be described in cooperation with a core sample 12 that is derived from a subterranean formation, and that is tested for particular properties that are important in evaluating subterranean oil reservoirs.

Core holder 10 is comprised, principally, of a core holding body 14 and a cap 30 disposed at one end thereof. Core holding body 14 is generally cylindrical and is provided with an internal chamber 20 for receiving sample 12. Screw threads 16 are disposed at one end of the core holding body and are adapted to mate with matching screw threads provided at one end of cap 30. As shown in FIG. 1, and as will be described further below, when cap 30 is secured to an end of core holding body 14, chamber 20 is defined by the interior wall of the core holding body and by the cap.

Suitable fittings 22 and 100 are provided in the side wall of the core holding body, these fitting being coupled to channels 24 and 98, respectively, each of which communicates with internal chamber 20. Fitting 22, and optionally fitting 100, is coupled to a source of "overburden", or confining pressure. Channel 24, and optionally channel 98, is adapted to supply suitably pressurized fluid to internal chamber 20, thereby supplying a confining pressure thereto.

Cap 30 is illustrated as being generally cylindrical and, as mentioned above, is provided with screw threads at one end thereof, whereby cap 30 is screwed onto a corresponding end of core holding body 14. Cap 30 is provided with a bore 33 in which is disposed a plug 32 secured to a body 34 by, for example, screws 37. A thrust washer 36 rests upon a shoulder 35 of body 34, and cap 30 bears against this thrust washer. An "O"-ring 40 in combination with an annular sealing element 50 cooperates with body 34 to seal the body to core holding body 14.

Plug 32 is provided with channels 42 and 44 therein, these channels communicating with sample 12 at one end thereof and with aligned channels 46 and 48 in body 34 at the other end thereof. "O"-rings 52 provide suitable seals at the interfaces of the respective channels. Channels 42, 46 and channels 44, 48 provide a passageway to supply fluid to one end of sample 12, this end, for convenience, being referred to as the upstream end of the sample. Suitable fittings (not shown) may be coupled to channels 46 and 48, respectively. If desired, body 34 (and plug 32) may be provided with only a single channel.

The upper end of cap 30, as illustrated in FIG. 1, includes a handle 78 to effect the securing of this cap to core holding body 14.

The bottom portion of chamber 20, as viewed in FIG. 1, is provided with a channel 60. A nut 62 is secured to the bottom end of core holding body 14 and a sealing member 64 is screwed through the threaded bore of this nut to urge packing 66 into channel 60. A tube 68 passes through sealing member 64 and packing 66 and extends upward through channel 60 for connection with a fitting 70 that is secured to a plug 72 having a channel 74 that communicates with sample 12. As shown, sample 12 is retained between plugs 32 and 72, referred to herein as the upstream and downstream plugs, respectively. As will be explained, fluid may be supplied from a suitable source (not shown), through channels 42, 46 and/or channels 44, 48 in upstream plug 32 to sample 12, and thence through channel 74 in downstream plug 72, fitting 70 and tube 68 to exit from core holding body 14. Concurrently, a confining fluid, of suitable overburden pressure, may be supplied to chamber 20 via fitting 22 and/or fitting 100, and channel 24 (and/or channel 98).

A flexible sleeve 80 is provided to receive core sample 12. In one embodiment, flexible sleeve 80 is comprised of a resiliently flexible material, such as plastic, and is adapted to retain the core sample under relatively high pressures. For example, the flexible sleeve may be formed as a laminate of suitable plastic materials, the inner layer of which is in contact with sample 12 being of relatively soft plastic material, and the outer-most layer being of relatively harder plastic material, such as heat shrinkable material. Alternatively, a thin coat of epoxy may be applied to the sample, and when dry, the epoxy-coated sample then may be inserted into a conventional rubber sleeve.

To assemble the illustrated core holder, a sample, preferably a cylindrical sample whose diameter may be on the order of 1 to 1½ inches, for example, and whose length may be on the order of about 3 inches, is retained between plugs 32 and 72. Flexible sleeve 80 is disposed about the sample and, as illustrated, also is disposed about at least portions of each of the plugs. Tube 68 is connected to. fitting 70 which, in turn, is attached to plug 72. Thus jacketed, sample 12, together with plugs 32 and 72 and tube 68, is inserted into chamber 20 of core holding body 14. Tube 68 is urged through channel 60 at the bottom of the core holding body, packing 66 and sealing member 64, the latter being screwed into nut 62 that is secured to the bottom of core holding body 14.

It may be appreciated that plug 32 may already be secured to body 34, and this combination is supported on the upper face of the core holding body and sealed thereto by sealing element 50 and O-ring 40. Then, thrust washer 36 is seated upon shoulder 35 of body 34 and cap 30 is screwed onto core holding body 14 by screw threads 16 to clamp the combination of plug 32 and body 34 to the core holding body, as illustrated.

Figure 2:
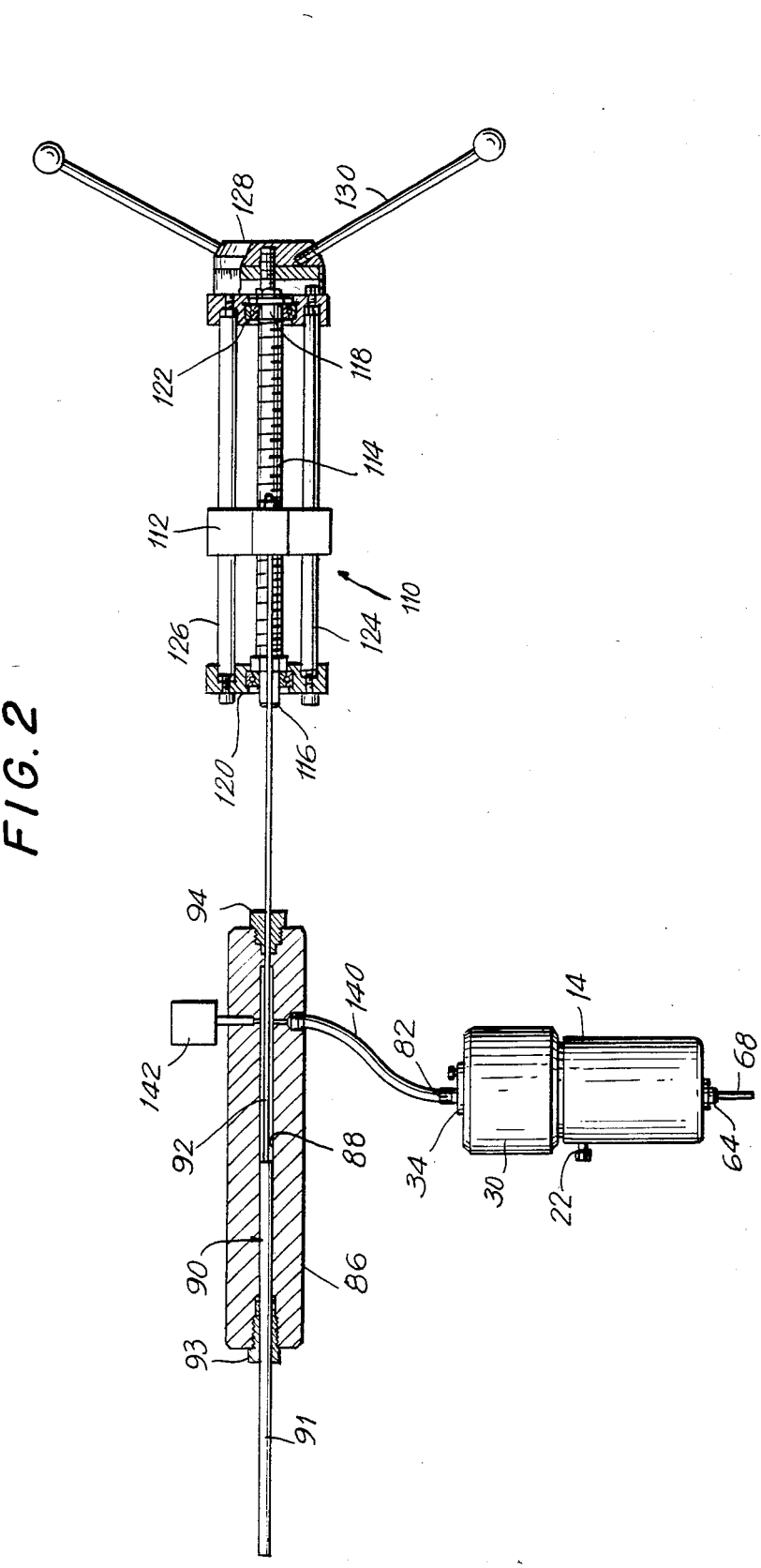
FIG. 2 is a sectional view of a preferred embodiment of an internal volume adjustment pump that is used with the core holder to test the compressibility of a sample.
Figure 3:
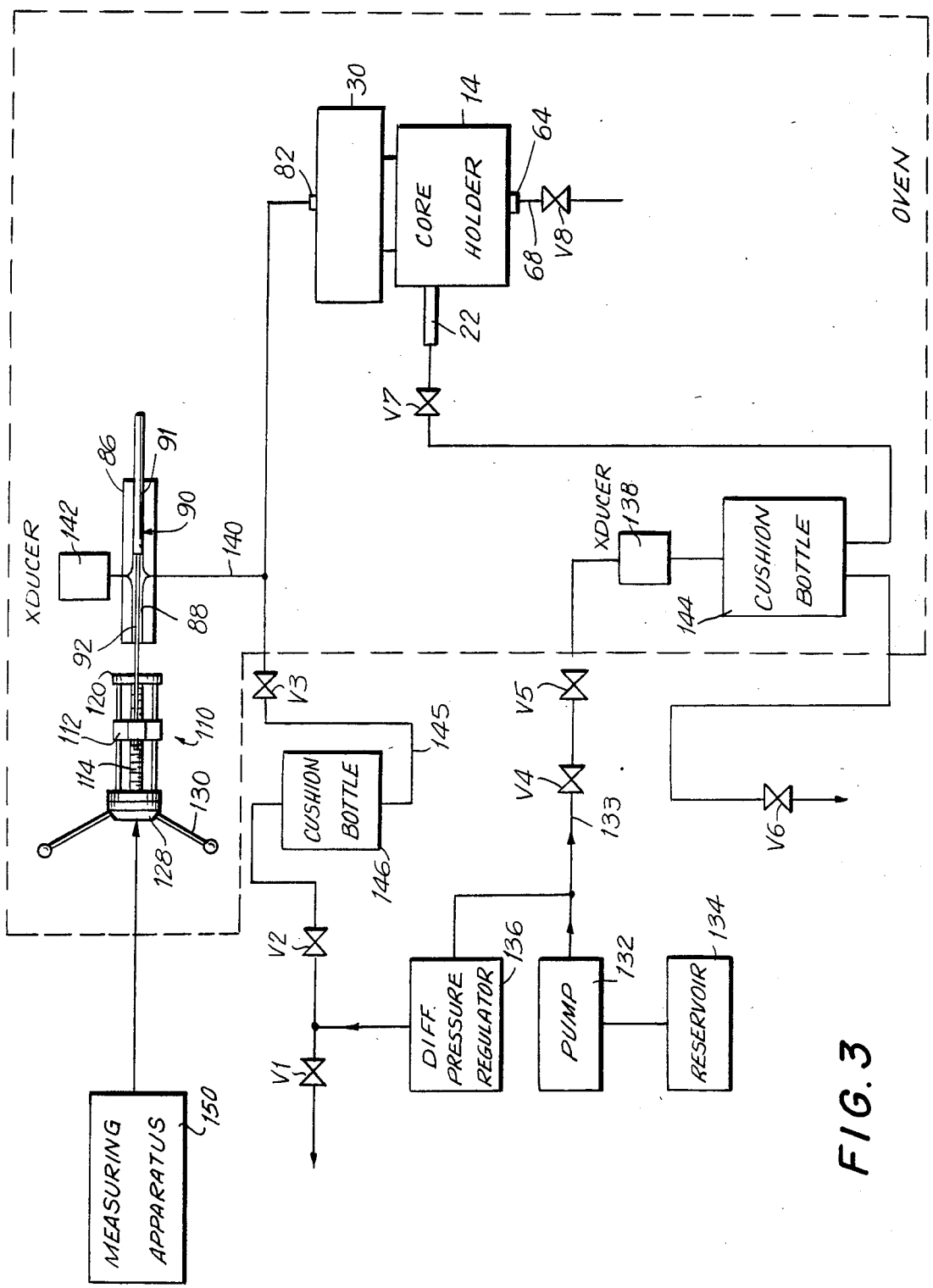
FIG. 3 is a schematic diagram of the fluidic system which uses the internal volume adjustment pump and core holder to carry out a compressibility test.

When core holder 10 is used to test the compressibility of a sample, the "internal volume" of the core holder, that is, the volume which includes the pore volume of sample 12, is varied while the confining pressure, that is, the pressure which surrounds the sample, is maintained relatively constant. This internal volume is varied by connecting the core holder to an internal volume adjustment pump, such as illustrated in FIG. 2. More particularly, a suitable fitting 82 is coupled to, for example, channel 46 in body 34. Channel 48 may be coupled to other fluidic apparatus, as shown in FIG. 3, or it may be sealed. It will be appreciated that, if desired, fitting 82 alternatively may be coupled to channel 48. In either embodiment, a tube or pipe 140 connects fitting 82 to the internal volume adjustment pump which, in the illustrated embodiment, is comprised of a housing 86 having an internal conduit 88 of fixed dimensions in which is disposed an axially movable differential piston 90 that is supported in sealing members 93 and 94 located at opposite ends of housing 86. Differential piston 90 is comprised of dual section rods of constant diameter, one section 91 having a relatively larger diameter and the other section 92 having a relatively smaller diameter.

It is recognized that the internal volume of the core holder in which sample 12 is disposed is comprised of the pore volume of the sample, the volume of channels 42, 46, the volume of channel 74 in plug 72, the volume of tube 68, the volume of tube or pipe 140 and the effective volume of channel 88 of housing 86. The effective volume of channel 88 and the entire internal volume system is displaced as a function of the relative position of differential piston 90 therein. As this piston moves from left-to-right (as viewed in FIG. 2), the effective volume of channel 88 is reduced because the larger diameter portion 91 of the piston displaces the internal volume of this channel. Conversely, as piston 90 moves from right-to-left, the effective volume of channel 88 is increased. It will be assumed that differential piston 90 is fully retracted when the larger diameter section 91 is at or in the vicinity of its right-most position.

Piston 90 is driven by a vernier 110 (FIG. 2) which is comprised of, for example, a rotatable lead screw 114 and a lead screw follower 112 to which the reduced diameter portion 92 of piston 90 is connected. Lead screw 114 is journaled for rotation in spaced apart bearings 116 and 118 located in opposite end blocks 120 and 122, respectively. Guide rails 124 and 126 are provided to guide the linear movement of follower 112 as lead screw 114 rotates. The lead screw is driven by a head 128 secured to one end thereof, this head being provided with handles 130 to permit manual rotation of the head and, thus, rotation of the lead screw. As illustrated, head 128 is provided with calibration indicia representing the rotary position of the lead screw and, thus, the position of follower 112 which, in turn, represents the position of differential piston 90 within channel 88. Since the position of the differential piston within channel 88 defines the effective volume of this channel, it is appreciated that the calibration indicia provided on head 128 may provide a correct indication of the effective volume of channel 88 and other connected components of the internal volume system. Other apparatus, described below, may be used to indicate, or measure, the effective volume of channel 88.

For a purpose to be explained below, a pressure transducer 142 is in communication with channel 88 via a suitable fluid communication passageway. It will be appreciated that pressure transducer 142 provides a measure, or indication, of the internal pressure of core holder 10. That is, transducer 142 provides an indication of the internal pressure that is applied to the pore-space of sample 12.

The pressure within channel 88 applies a force to differential piston 90. Advantageously, the connection of the reduced diameter portion 92 of piston 90 to lead screw follower 112 results in the application of tension to the stressed area of the piston rather than the application of compression thereto. Consequently, the danger of buckling, which would be present if a piston of uniform diameter is used, is obviated. Hence, operational safety is improved. Moreover, by using a differential piston, higher internal pressures may be applied, and the internal pressure that is supplied to the sample may be increased during a compressibility test. This is an improvement over devices in which the compressibility test is dependent only upon reductions in internal pressure. Hence, by using the differential piston shown in FIG. 2, actual reservoir conditions may be simulated, such as when the pressure applied to a subterranean formation is increased due to, for example, water injection of partially depleted reservoirs. Also, the use of differential piston 90 permits accurate evaluation of reservoirs for gas storage projects.

The manner in which core holder 10 and the internal volume adjustment pump are used to determine the compressibility of a subterranean sample now will be described with reference to the fluidic schematic diagram illustrated in FIG. 3. Preferably, the core holder, internal volume adjustment pump and internal and confining pressure transducers are disposed in an oven which maintains a substantially constant temperature that may be selected in the range of ambient to 125° F.±0.2° F. A high pressure saturation pump 132 is coupled to a suitable fluid reservoir 134 to supply pressurized fluid to the core holder. A fluid channel, such as a hose or tube 133, is provided with valves V4, V5 and V7 to connect the pressurized fluid supplied from pump 132 to, for example, fitting 22 for the purpose of supplying a confining pressure to the sample within chamber 20 of the core holder. A pressure transducer 138 is disposed in fluid channel 133 to provide an indication of the confining pressure that is applied to the sample. As is conventional, a cushion bottle 144 also is provided in fluid channel 133, and a valve V6 is connected to an overflow outlet of this cushion bottle.

A differential pressure regulator 136 is coupled to pump 132 and is adapted to supply a fluid, whose pressure is reduced from the confining pressure, to sample 12 within chamber 20 of core holder 10. A fluid channel, such as a hose or tube 145, connects the output of the differential pressure regulator to, for example, fitting 82 of the core holder. A conventional T connection is used to connect fluid channel 145 to channel 88 of the internal volume adjustment pump and also to fitting 82. Alternatively, fluid channel 145 may be connected to channel 48 of the core holder, with channel 46 in the core holder being connected by tube 140 to channel 88 of the internal volume adjustment pump. Valves V2 and V3 are provided in fluid channel 144, and a conventional cushion bottle 146 also is provided in this channel.

In testing the compressibility of a sample, that sample preferably should be formed as a right cylinder with a diameter of 1 inch to 1½ inches and length of approximately 3 inches. Prior to being jacketed in flexible sleeve 80 (FIG. 1), it should be subjected to those nondestructive tests which are desired. Sample 12 may be jacketed in the manner described above, and then it is loaded into chamber 20 of core holder 10.

Before loading the jacketed sample into the core holder, a measurement of the effective internal volume of the core holder should be carried out. This internal volume, as stated above, is comprised of the pore volume of the sample to be tested, together with the volume of tube 68, channel 42, 46, tube 140 and the effective volume of channel 88 of the internal volume adjustment pump. It will be recognized that the effective internal volume of the core holder also includes the volume of those lengths of fluid channels which may extend to, for example, valve V3 and to valve V8 (FIG. 3).

The aforementioned effective internal volume of the core holder, referred to herein as the internal system volume, is measured by loading a plug of known material, such as a stainless steel plug, of the same nominal diameter as the sample to be tested, into chamber 20. This stainless steel plug preferably includes a relatively small channel therethrough, such as on the order of 1/16 inch diameter, and it is jacketed with a flexible sleeve similar to sleeve 80. Additionally, plugs 32 and 72 (FIG. 1) are located at opposite ends of this stainless steel plug, with channels 74 and 42 in alignment with the channel through the stainless steel plug. Initially, the effective volume of channel 88 of the internal volume adjustment is minimized. This is achieved by fully retracting differential piston 80 within housing 86. Thus, the larger diameter portion 91 of piston 90 substantially fills channel 88.

A helium porosimeter is connected to valve V8 (FIG. 3) downstream of core holder 10. At this time, valve V3, which functions as an internal cut-off valve, is closed; and a suitable overburden pressure is supplied via valve V7 and fitting 22 to chamber 20. Thus, a confining pressure is applied to the jacketed stainless steel plug held within core holder 10. The porosimeter measures the total internal system volume. It is recognized that this measured volume includes the volume of the channel within the stainless steel plug and also the volume of the tube by which the porosimeter is connected to valve V8. These volumes, which are known and are constant, should be subtracted from the measured volume, thus resulting in the "dead" volume of the internal system. The effective internal system volume is, of course, equal to this "dead" volume plus the pore volume of sample 12.

Next, the stainless steel plug is removed from chamber 20 and is replaced by jacketed sample 12 having plugs 32 and 72 positioned at its opposite ends. Before cap 30 is screwed into place on core holding body 14, the annular space in chamber 20 surrounding the jacketed, plugged sample is filled with a fluid, such as water. Cap 30 then is screwed into place, and a confining pressure on the order of about 200 psi is applied via fitting 22 to seal sleeve 80 about sample 12.

To assure a substantially constant temperature during the compressibility test, the oven should be set to a desired temperature. Although not shown, it will be appreciated that suitable electrical heating controls are provided to maintain the oven temperature constant at its preset level.

In place of the helium porosimeter which was used to measure the internal "dead" volume, a vessel containing brine is connected to downstream valve V8. A suitable vacuum source is coupled to valve V1, and valves V1, V2, V3 and V8 are opened. Preferably, the remaining valves are closed. By reason of the vacuum source (for example, a source supplying a pressure that is less than 0.2 psi), brine flows from the vessel through valve V8, tube 68, channel 74, sample 12, channel 42, 46, valve V3, fluid channel 145 and valves V2 and V1. It is appreciated that brine also will flow through and fill the effective volume of channel 88 of the internal volume adjustment pump. This continues until the internal system volume, including the pore volume of sample 12, is saturated. For samples having relatively low permeability (e.g. on the order of less than 15 md), an accumulator, such as a floating piston accumulator, may be needed in addition to the vacuum source in order to saturate the sample properly.

After sample 12 has been saturated, differential pressure regulator 136 is connected between valves V1 and V2 (as illustrated in FIG. 3). The differential pressure regulator supplies an output pressure that varies with the pressure provided by pump 132. Preferably, this output pressure varies linearly with the pressure provided by the pump; and in the embodiment described herein, the output pressure of the differential pressure regulator is 200 psi less than the pump pressure. The output pressure of the differential pressure regulator maintains this linear relationship with the pump pressure up to about 10,000 psi. The pressure provided by pump 132 is supplied to core holder 10 as the confining pressure for sample 12, and the pressure provided by differential pressure regulator 136 is supplied to the core holder as the internal pressure for this sample. The differential pressure regulator functions to maintain the aforementioned 200 psi pressure differential between the confining and internal sample pressures.

Valves V1 and V8 are closed, and valves V2 and V3 are opened to supply the internal pressure to sample 12. Concurrently, valve V6 is closed and valves V4, V5 and V7 are opened to supply the confining pressure to this sample from pump 132. The confining and internal pressures are raised at the rate of 250 psi per minute. The sample thus has time to adjust to the changing stresses applied thereto.

After the desired maximum confining and internal pressures are reached, for example, a maximum confining pressure on the order of 10,000 psi, valves V2 and V4 are closed to maintain these pressures constant. Prior to beginning the compressibility test on sample 12, the sample should be stabilized for a predetermined time, for example, approximately 30 minutes. The internal pressure is considered stabilized if it does not change by more than one psi in a five-minute interval.

At the beginning of the compressibility test, the effective volume of channel 88 is recorded. As mentioned above, channel 88 should exhibit its minimum volume, which is achieved when the larger diameter portion 91 of piston 90 is fully retracted. The recording of the effective volume of channel 88 may be carried out automatically, as by electronic means for measuring the rotary position of head 128, or manually. As an example, measuring apparatus 150 may be coupled to head 128 to measure the position thereof. In the embodiment wherein the measuring apparatus is comprised of electronic means, it may include an encoder, such as an angle or linear encoder or other conventional position measuring means providing an analog or digital signal indicative of the position of piston 90 or head 128 and, thus, of the effective volume of channel 88. As an alternative embodiment, measuring apparatus 150 may comprise mechanical means known to those of ordinary skill in the art for measuring, or indicating, the position of piston 90 or head 128. Such mechanical means may include a linear or rotary scale to provide a reading or other indication (e.g. a mechanical displacement) of the effective volume of channel 88.

The compressibility test then is carried out by increasing the internal system volume in predetermined increments. In particular, such incremental volume increases are obtained by rotating head 128 a predetermined amount which, in turn, advances the reduced diameter portion 92 of differential piston 90 in channel 88. By increasing the internal volume, a corresponding decrease in internal pressure is attained. Pressure transducer 142 measures the internal pressure, and a reading of this transducer may be used to reduce the internal pressure in predetermined steps on the order of 500 to 1,000 psi increments. The increase in internal volume $\Delta V$ for each incremental change in internal pressure $\Delta P$ (i.e. for each 500 to 1,000 psi pressure decrease) is recorded or measured by apparatus 150. Although the internal pressure is reduced by reason of the increase in internal system volume, it is appreciated that the confining pressure applied to sample 12 remains constant. Thus, the net confining pressure, which is equal to the difference between the applied confining pressure and the sample pore pressure, increases as the internal system volume increases. Although the internal system volume increases by increasing the effective volume of channel 88 of the internal volume adjustment pump, the increase in net confining pressure results in a decrease in the sample pore volume. The reduced sample pore volume may be calculated by subtracting the change in the effective volume of channel 88 from the initial sample pore volume for each 500 to 1,000 psi change in the internal pressure. This calculation, however, should be adjusted for correction by taking into account the increase in the volume of the test fluid (assumed to be brine) due to its compressibility and also by taking into account the slight change in volume of the test equipment due to elastic deformation of the components which are exposed to the relatively high pressures. The increase in test fluid volume due to its compressibility (i.e. because of the expansion of the test fluid as the pore pressure decreases) can be calculated and the correction for equipment volume change can be determined following the compressibility test of the sample, as will be described below.

The change in pore volume resulting from the increase in effective overburden pressure may be calculated from the following relationship:

The pore volume of the sample at initial net confining pressure (e.g. the effective confining pressure of 200 psi), which is measured initially;

MINUS

The increase in internal volume (i.e. the increase in effective volume of channel 88)

PLUS

The increase in test fluid volume because of the expansion of the test fluid as the pore pressure (i.e. internal pressure) decreases

PLUS

Correction for changes in the volume of the apparatus

EQUALS

The pore volume of the sample at the present net confining pressure.

As the net confining pressure increases, preferably in 500 psi increments, by advancing piston 90 through conduit 88, the decrease in pore volume as a function of this net confining pressure increase may be calculated by using the foregoing relationship, and the resulting data may be graphically represented. The resultant curve, which represents the relationship of sample pore volume as a function of increasing net confining pressure, then may be used to obtain the compressibility of the sample, this compressibility being obtained in terms of $\Delta PV/PV.psi$, wherein $\Delta PV$ is the change in pore volume, and psi is the net confining pressure. It is preferred not to reduce the internal pressure (that is, the pore pressure of sample 12) below about 300 psi. The calculated compressibility represents hydrostatic compressibility. In the subterranean formation from which sample 12 is derived, the actual compressibility is uniaxial compressibility. As is known, the calculated hydrostatic compressibility data may be converted to corresponding uniaxial compressibility data merely by multiplying the hydrostatic data by the factor 0.619.

It will be appreciated that by establishing an initially high confining pressure (e.g. on the order of about 10,000 psi), and a correspondingly high internal pressure (e.g. on the order of about 9,800 psi), and then by reducing the internal pressure, sample 12 is subjected to conditions which closely simulate the actual conditions present in the subterranean formation when oil is extracted therefrom. That is, as oil is extracted, the internal pressure of the subterranean formation attributed to the pressure of the oil reservoir, is reduced. Of course, the external, or confining pressure, remains at its fixed, high level. Consequently, the compressibility of the sample based upon the measured changes in internal pressure and internal volume is more accurate than techniques which heretofore measured compressibility by increasing the confining pressure in successive increments. Nevertheless, since the reduced diameter portion 92 of piston 90 can be driven easily out of channel 88 of the internal volume adjustment pump so as to decrease the effective volume of the channel and increase the internal pressure, sample pore volume data can be obtained by decreasing the net confining pressure in predetermined (e.g. 500 psi) increments.

The aforementioned corrections for changes in the volume of the compressibility test apparatus are determined by subjecting a plug of rigid material (such as the aforementioned stainless steel plug) to the same test as that which was used to test the compressibility of sample 12. This apparatus volume-change correction is determined by jacketing a stainless steel plug of approximately the same length and diameter of the sample tested, and locating this jacketed plug between plugs 32 and 72 in chamber 20 of core holding body 14. To allow fluid saturation of the internal system volume, the stainless steel plug is provided with a channel having a diameter of, for example, 1/16 inch, along its vertical axis. It is assumed that the equivalent "pore" volume of this stainless steel plug, that is, the volume of its channel, is known in advance, either from measurement or from manufacturer's specifications.

After the internal system volume has been saturated, a compressibility test is carried out in the manner described above. For example, a confining pressure on the order of 10,000 psi and an internal pressure on the order of 9,800 psi are applied to the stainless steel plug "sample". Differential piston 90 of the internal volume adjustment pump is fully retracted and the pore volume of the stainless steel "plug" at initial net confining pressure is measured. Then, the reduced diameter portion 92 of piston 90 is driven into channel 88 to reduce the internal system pressure by increments of, for example, 500 psi. With each such incremental decrease in the internal system pressure (resulting in a corresponding incremental increase in the net confining pressure), the "pore" volume of the stainless steel plug is calculated. Of course, since this pore volume is equal to the volume of the 1/16 inch channel therein and, thus, remains constant, any change in the calculated "pore" volume is attributed to changes in the volume of the apparatus. That is, if the calculated "pore" volume for the stainless steel plug at a particular net confining pressure is less than the actual volume of the channel in this plug, this difference between the calculated and actual "pore" volumes should be added to the calculated pore volume of the sample that had been tested at that particular net confining pressure. Such apparatus volume-change corrections are substantially constant for a given core holder, internal volume adjustment pump, particular confining and internal pressures and sample diameter. Hence, the test run for determining the apparatus volume-change corrections may be carried out only once, provided the same conditions (e.g. the same incremental changes in the net confining pressure, the same sample diameter and the same maximum confining pressure) are used for each sample test run.

While the present invention has been particularly shown and described with reference to a certain preferred embodiment, it should be readily apparent to those of ordinary skill in the art that various changes and modifications may be made without departing from the spirit and scope of the invention. It is intended that the scope of this invention be limited solely by the appended claims, and that these claims be interpreted so as to include all such changes and modifications. This invention is not intended to be limited solely to the embodiments illustrated herein.

What is claimed is:

1. Compressibility test apparatus comprising holder means having a sample chamber for holding a sample whose compressibility is to be tested, said holding means having a confining pressure inlet for receiving a confining pressure to be applied to said sample, an internal pressure inlet for receiving an internal pressure to be applied to said sample, an internal pressure outlet, and respective channels between said sample in said chamber and said internal pressure inlet and outlet; said respective channels in combination with said internal pressure inlet, said internal pressure outlet and said sample chamber exhibiting a volume; means for supplying a substantially constant pressure to said confining pressure inlet; and means for varying said volume, including a conduit of substantially constant dimensions, means for coupling said conduit to said volume, and means for selectively adjusting the volume of said conduit, thereby changing the internal pressure applied to said sample as said volume is adjusted, the change in said internal pressure being inversely related to the adjustment of said volume.

2. The apparatus of claim 1 wherein said means for selectively adjusting the volume of said conduit comprises a differential piston movable axially in said conduit.

3. Compressibility test apparatus comprising holder means having a sample chamber for holding a sample in the environment of a confining pressure, said sample having a pore volume; confining pressure supply means for supplying a confining pressure to said sample; internal pressure supply means for supplying an internal pressure to said sample separate from said confining pressure, said sample pore volume and the volume of said internal pressure supply means being included in an internal system volume; a channel coupled to and includable in said internal system volume, a differential piston having a first section of larger cross-sectional area and a second section of smaller cross-sectional area, the first and second sections of said differential piston both being movable in said channel; and drive means for driving said differential piston to vary the proportion of the first and second sections thereof within said channel and thereby vary said internal system volume.

4. The apparatus of claim 3 wherein said holder means includes a channel communicating with the sample in said chamber to supply said internal pressure to said sample; and further comprising means for providing fluid communication between the last-mentioned channel in said holder means and the channel in which said differential piston moves.

5. The apparatus of claim 3 wherein said drive means comprises vernier adjustment means.

6. The apparatus of claim 5 wherein said vernier adjustment means comprises a longitudinal, rotatable lead screw; lead screw follower means mounted on said lead screw and movable along the length of said lead screw as said lead screw rotates, the lead screw follower means being connected to said differential piston; and means for rotating said lead screw.

7. The apparatus of claim 6 wherein said means for rotating said lead screw comprises a rotatable head secured to said lead screw; and handle means coupled to said head.

8. The apparatus of claim 7 further comprising at least one guide rail disposed parallel to said lead screw for guiding said lead screw follower means.

9. The apparatus of claim 6 wherein said lead screw follower means is connected to said second section of said differential piston.

10. Compressibility test apparatus comprising holder means having a sample chamber for holding a sample in the environment of a confining pressure, said sample having a pore volume; confining pressure supply means for supplying a confining pressure to said sample; internal pressure supply means for supplying an internal pressure to said sample separate from said confining pressure, said sample pore volume and the volume of said internal pressure supply means being included in an internal system volume; internal volume adjustment means comprising a channel coupled to and includable in said internal system volume, a differential piston having a first section of larger cross-sectional area and a second section of smaller cross-sectional area, said differential piston being movable in said channel, and drive means connected to said second section of said differential piston and operable to retract said first section into said channel initially to minimize said internal system volume, whereby said internal pressure exerts a tension force on said differential piston, said drive means being further operable during a test to advance said second section of said differential piston into said channel to increase said internal system volume and thereby decrease said internal pressure.

11. The apparatus of claim 10 wherein said drive means comprises a rotary head and means for converting rotary motion of said head to translational motion of said differential piston, said head being provided with indicia to select incremental increases in said internal system volume.

12. The apparatus of claim 10, further comprising a source of pressurized fluid; means for coupling said source of pressurized fluid to said confining pressure supply means; differential pressure regulating means coupled to said source of pressurized fluid to produce at its output a reduced pressure that is less than but linearly related to the pressure of said pressurized fluid; and means for coupling the output of said differential pressure regulating means to said internal pressure supply means.

13. The apparatus of claim 12 wherein said internal pressure initially is less than said confining pressure by a predetermined amount; and further comprising means operable during a test to maintain said confining pressure constant.

14. The apparatus of claim 10 further comprising measuring means coupled to said internal volume adjustment means for measuring changes in the effective volume of said channel by the movement of said differential piston therein.

15. The apparatus of claim 14 wherein said measuring means comprises a scale for providing a mechanical indication of said changes in the effective volume of said channel.

16. The apparatus of claim 15 wherein said scale comprises a linear scale.

17. The apparatus of claim 15 wherein said scale comprises a rotary scale.

18. The apparatus of claim 14 wherein said measuring means comprises encoder means for providing an electrical indication of said changes in the effective volume of said channel.

19. The apparatus of claim 18 wherein said electrical indication includes an electrical analog signal output.

20. The apparatus of claim 18 wherein said electrical indication includes a digital signal output.

21. A method for use in testing the compressibility of a sample of a subterranean geological formation, comprising the steps of supplying a fixed confining pressure environment in which said sample is disposed, said confining pressure having a magnitude approximating the confining pressure of said subterranean geological formation; applying an internal pressure to said sample via an internal fluid supply in communication with said sample, the internal volume of said internal fluid supply including the pore volume of said sample, and said internal pressure initially being less than said confining pressure by a predetermined amount; increasing said internal volume to cause a corresponding decrease in, said internal pressure of said sample by a predetermined amount; and measuring the increase of said internal volume which results in said predetermined decrease in internal pressure.

22. The method of claim 21 further comprising the step of saturating said sample with a test fluid prior to supplying a fixed confining pressure.

23. A method for use in testing the compressibility of a sample of a subterranean geological formation, comprising the steps of supplying a fixed confining pressure environment in which said sample is disposed, said confining pressure having a magnitude approximating the confining pressure of said subterranean geological formation; applying an internal pressure to said sample via an internal fluid supply in communication with said sample, the internal volume of said internal fluid supply including the pore volume of said sample, and said internal pressure initially being less than said confining pressure by a predetermined amount; increasing said internal volume to cause a corresponding decrease in said internal pressure of said sample by a predetermined amount, said confining pressure being maintained fixed while said internal pressure is decreased; determining the initial pore volume of said sample when said internal pressure is less than said confining pressure by said predetermined amount, and determining the change in the pore volume of said sample by subtacting from said initial pore volume the increase in said internal volume and measuring the increase of said internal volume which results in said predetermined decrease in internal pressure.

24. The method of claim 21 wherein said internal volume is increased by moving a differential piston through a channel of predetermined dimensions that is included as a part of said internal volume.

25. A method for use in testing the compressibility of a sample of a subterranean geological formation, comprising the steps of (a) saturating said sample with a liquid; (b) measuring an initial pore volume of said sample; (c) supplying a fixed confining pressure environment in which the saturated sample is disposed, said confining pressure having a magnitude approximating that of the confining pressure of said subterranean geological formation; (d) applying an internal pressure to the saturated sample, the internal pressure being separate from said confining pressure and initially being less than said confining pressure by a predetermined amount; (e) increasing the internal volume in communication with said sample and through which said internal pressure is applied to cause a corresponding decrease in said internal pressure by a predetermined amount, said internal volume including as a part thereof the pore volume of said saturated sample; (f) measuring the increase of said internal volume which results in said predetermined decrease in internal pressure; and (g) repeating steps (e) and (f).

26. The method of claim 25, further comprising the step of (h) determing the pore volume of said sample at each predetermined decrease in internal pressure by subtracting from said initial pore volume the increase in said internal volume and correcting for volume changes in the compressibility test apparatus.

27. The method of claim 26 wherein said step of correcting for volume changes in the compressibility test apparatus comprises repeating steps (a) through (h) with a plug of constant known pore volume and of approximately the same dimensions as the tested sample and noting at each predetermined decrease in internal pressure the difference between the determined pore volume of said plug and actual pore volume thereof and using each said difference to correct a respective determined pore volume of said sample.

28. The method of claim 27 wherein said step (h) of determining the pore volume of said sample further includes the step of adding to said initial pore volume an increase in the volume of said liquid caused by the compressibility thereof.

* * * * *